(12) United States Patent
Knight et al.

(10) Patent No.: US 6,935,159 B2
(45) Date of Patent: Aug. 30, 2005

(54) CENTRIFUGAL PERMEAMETER

(75) Inventors: Mark A. Knight, Waterloo (CA); Shayne Giles, Waterloo (CA)

(73) Assignee: University of Waterloo, Waterloo (CA)

( * ) Notice: Subject to any disclaimer, the term of this patent is extended or adjusted under 35 U.S.C. 154(b) by 156 days.

(21) Appl. No.: 10/715,429

(22) Filed: Nov. 19, 2003

(65) Prior Publication Data

US 2005/0103094 A1 May 19, 2005

(51) Int. Cl.$^7$ .................................. G01N 15/98
(52) U.S. Cl. ................................... 73/38
(58) Field of Search ............................ 73/38

(56) References Cited

U.S. PATENT DOCUMENTS

| | | | |
|---|---|---|---|
| 3,839,899 A | | 10/1974 | McMillen |
| 4,562,726 A | * | 1/1986 | Barnaby ..................... 73/38 |
| 4,671,102 A | | 6/1987 | Vinegar et al. |
| 4,679,422 A | | 7/1987 | Rubin et al. |
| 5,297,420 A | | 3/1994 | Gilliland et al. |
| 5,325,723 A | | 7/1994 | Meadows et al. |
| 5,563,333 A | | 10/1996 | Haines et al. |
| 5,783,760 A | | 7/1998 | Haines et al. |
| 6,185,985 B1 | | 2/2001 | Fleury et al. |

FOREIGN PATENT DOCUMENTS

| | | | | | |
|---|---|---|---|---|---|
| FR | 2758881 A | * | 7/1998 | .......... | G01N/27/07 |
| GB | 2325526 A | * | 11/1998 | .......... | G01N/15/08 |

* cited by examiner

Primary Examiner—Hezron Williams
Assistant Examiner—John Fitzgerald
(74) Attorney, Agent, or Firm—Gowling Lafleur Henderson LLP; Peter Milne

(57) ABSTRACT

The present invention provides a sample chamber for a centrifugal permearmeter for testing permeant conductivity of a porous sample, the sample chamber comprising a rigid outer sleeve; a resilient inner sleeve mountable over the sample and within the rigid outer sleeve; fluid inlet means for introducing fluid between the inner and outer sleeves; sealing means acting between the inner and outer sleeves for maintaining the fluid therebetween; a porous top member for mounting over a top face of the sample and supplying the permeant to the sample, the top being movable with the sample to maintain a radially outward permeant force on the sample as the sample is being spun in the centrifugal permeameter; a permeant supply for supplying the permeant to the porous top; and, a permeant accumulator for receiving and accumulating permeant which has passed through the sample.

14 Claims, 13 Drawing Sheets

Comparison of Triaxial and Centrifuge Hydraulic Conductivity

CENTRIFUGAL PERMEAMETER

The present invention relates to testing and modelling the hydrodynamic properties of stress sensitive samples with a centrifugal permeameters.

BACKGROUND OF THE INVENTION

Prescriptive landfill legislation, guidelines and directives presently limit the hydraulic conductivity of compacted soil liners to $1\times10^{-7}$ cm/s or lower. Presently sample testing liners can require between five and fourteen testing days when tested according to procedures specified by American Standard Test Method (ASTM) 5084-D. As a result of the long test times large sections of field compacted liners are not directly tested for hydraulic compliance. Present flexible wall bench testing techniques are time prohibitive and equipment intensive (samples must be transported to a laboratory for testing). Furthermore there is a lack of government and industry education.

A permeameter is used to determine the fluid transport properties of a porous medium. e.g. a compacted soil layer. A current method of testing employs a static bench permeameter with a hydraulic head applied via a pressure system. This type of testing requires a significant capital expenditure to implement, resulting in a significant per sample cost. Also the results are often untimely and are based on the questionable quantification of very small outflow volumes measured over short time periods. For impermeable samples (generally materials with a hydraulic conductivity less than $1\times10^{-7}$ cm/s) augmentation steps may be employed to increase the amount of outflow volume over a shorter time period by applying a substantial fluid head to the sample either by a column of fluid or a pressurized system. This augmentation can result in the testing of samples with high fluid gradients and high fluid pressures within the sample.

Rigid wall centrifuge permeameters provide faster results and are potentially mobile. A problem that remains is how to seal the sample against the rigid sleeve so that fluid does not pass between the sample and the wall. Compacting the sample does not solve the problem—the sample is no longer in its natural state and the potential for leakage remains. However, the rigid wall construction of the permeameter may results in the testing liquid leaking past the sample along the rigid wall. This is particularly a concern.

It is an object of the present invention to provide a permeameter to obviate or mitigate at least some of the above presented disadvantages.

SUMMARY OF THE INVENTION

According to the present invention there is provided a sample chamber for a centrifugal permeameter for testing permeant conductivity of a porous sample, the sample chamber comprising a rigid outer sleeve; a resilient inner sleeve mountable over the sample and within the rigid outer sleeve; fluid inlet means for introducing fluid between the inner and outer sleeves; sealing means acting between the inner and outer sleeves for maintaining the fluid therebetween; a porous top member for mounting over a top face of the sample and supplying the permeant to the sample, the top being movable with the sample to maintain a radially outward permeant force on the sample as the sample is being spun in the centrifugal permeameter; a permeant supply for supplying the permeant to the porous top; and, a permeant accumulator for receiving and accumulating permeant which has passed through the sample.

The sample chamber may further include a sensor for sensing changes in at least one of pressure and volume in the fluid between the inner and outer sleeves and sending a signal to a receiver indicative of the volume change during centrifuging.

The sample chamber may also have a sensor in the accumulator for determining an amount of the permeant which has permeated the sample and sending a signal to a receiver indicative of the amount during centrifuging.

The sample chamber may further have a sensor in fluid communication with the permeant supply for sensing pressure exerted by the permeant on the sample and sending a signal to a receiver indicative of the exerted permeant pressure during centrifuging.

The sample chamber may additionally include a sensor for determining a degree of sample consolidation exhibited by the sample during centrifuging and sending a signal to a receiver indicative of the degree of sample consolidation during centrifuging.

In a further embodiment, the sample chamber further comprises comparing and adjusting means for comparing the changes in the at least one of pressure and volume of the fluid between the inner and outer sleeves to the pressure exerted by the permeant on the sample and adjusting the at least one of pressure and volume of the fluid between the inner and outer sleeves by a degree sufficient to restrict movement of the permeant to the porous sample.

The rigid outer sleeve may be comprised of one of plastic, metal and glass.

The resilient inner sleeve may be comprised of latex.

The porous top member may comprise a top cap and an underlying porous material having a permeant conductivity greater than that of the sample.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
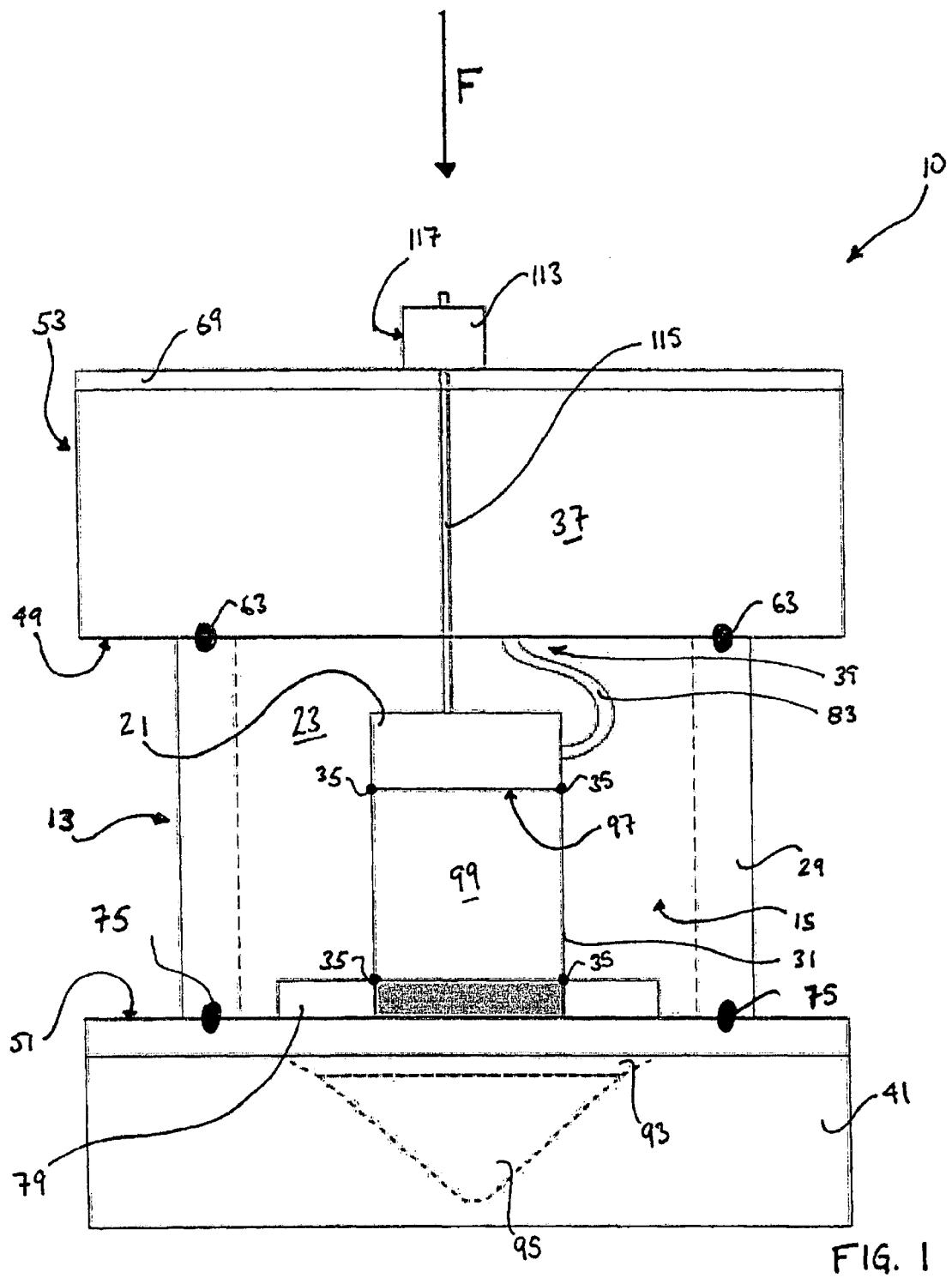
FIG. 1 is a cross-sectional view of a sample chamber according to an embodiment of the present invention.

Referring to FIG. 1, a schematic cross-sectional view of a sample chamber 10 for a centrifugal permeameter for testing permeant conductivity of a porous sample 99 is illustrated. The sample chamber 10 has a confining chamber 13 having a rigid outer wall or sleeve 29 and a resilient inner sleeve 31 mountable over the sample 99. The inner sleeve 31 is positioned within the outer sleeve 29. The chamber 10 has fluid inlet means 33 for introducing a confining fluid 23 between the inner and outer sleeves (31, 29) and sealing means 35 acting between the inner and outer sleeves (31, 29) for maintaining the fluid 23 therebetween. A porous top member 21 mounts over a top face 97 of the sample 99 to supply a permeant 37 to the sample 99. The top member 21 is moveable with the sample 99 to maintain a radially outward permeant force on the sample 99 as the sample 99 is being spun in the centrifugal permeameter. A permeant supply 39 is provided for supplying the permeant 37 to the top 21; and, a permeant accumulator 41 is provided for receiving and accumulating permeant 37 which has passed through the testing sample 99.

Figure 2:
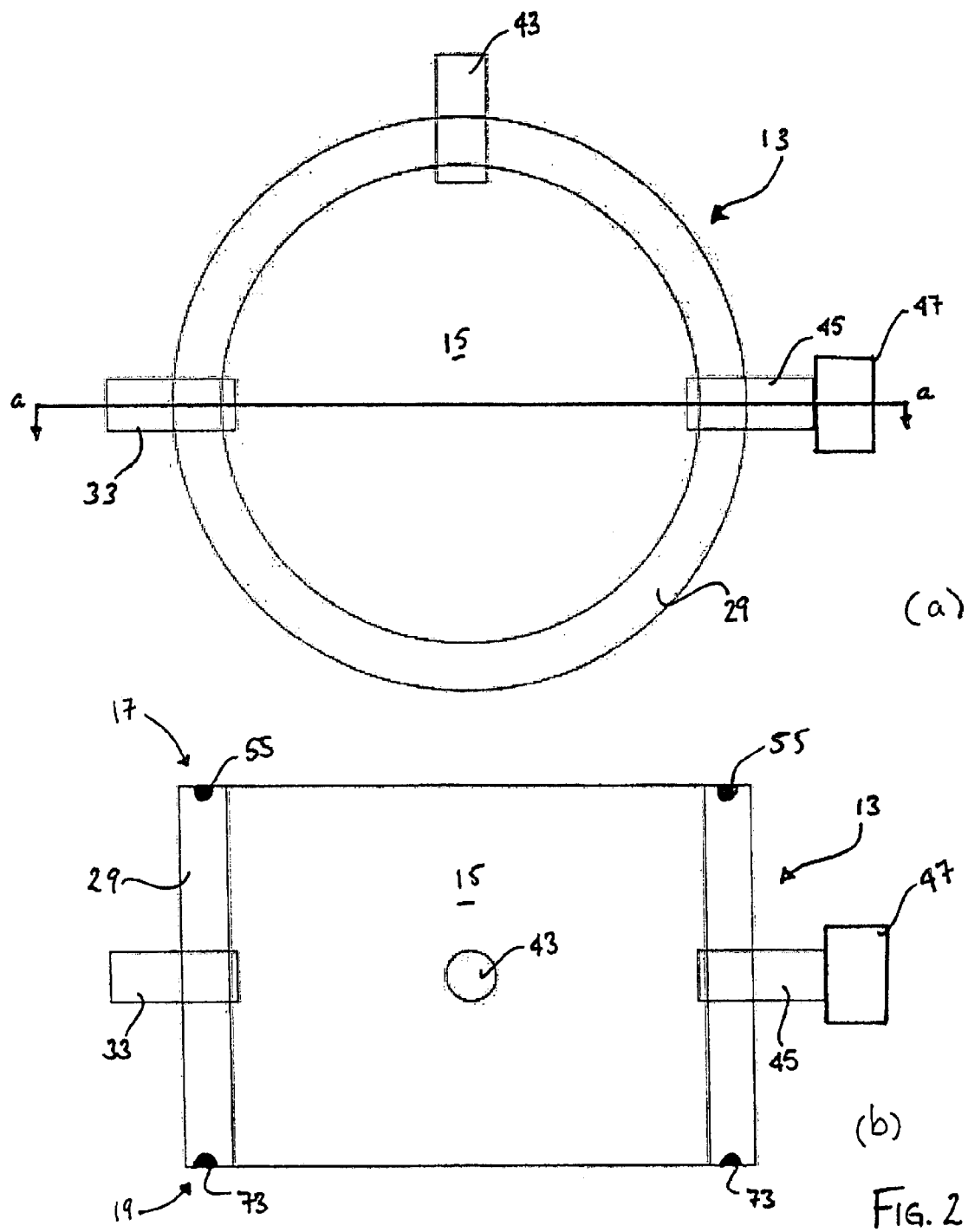
FIG. 2(a) is a plan view of a confining chamber of the apparatus of FIG. 1 according to an embodiment of the present invention.
FIG. 2(b) is a sectional view of the confining chamber of (a)

Referring to FIGS. 1 and 2, the confining chamber 13 in a preferred embodiment is generally cylindrical in shape, the outer rigid walls 29 of which, defining its outer perimeter. The outer rigid walls 29 are constructed of a material having sufficient mechanical strength to resist significant pressure changes of the fluid 23 during sample 99 testing. The outer walls 29 may be comprised of a clear material (such as a plastic or glass) so as to permit viewing of the sample 99 during testing. Alternately, the rigid walls 29 may be comprised of a metal, such as aluminium, stainless steel, copper, nickel or any allow thereof. In a still further embodiment, the rigid walls 29 may also include a clear window to permit viewing of the sample 99 during the testing. Any material known to those skilled in the art that has sufficient material strength to withstand fluid 23 volume and pressure changes during sample 99 testing may be employed.

The rigid outer wall 29 further includes connection ports that permit outside access to the interior of the chamber 13. In a preferred embodiment, the wall 29 includes three ports: a fluid inlet means or fill port 33 that permits the addition of confining fluid 23 to the chamber 13; an exhaust port 43 for removing air from the chamber 13; and, a monitoring port 45 for fluidly communicating with a pressure measuring device or sensor 47 connected to the wall 29 for monitoring the pressure of the internal confining fluid 23 in of the chamber 13. In a preferred embodiment, the ports 33, 43 and 45 include one-way valves to prevent loss of confining fluid 23 from chamber 13 or addition of air to chamber 13.

Fill port 33 and exhaust port 43 are preferably quick connect fittings, as is known to those skilled in the art, such as the Dehrin Acetal PMC Series 10 quick connect ports as manufactured by the Colder Products Company of St. Paul, Minn. USA. However, any suitable quick connect port known to those skilled in the art may be employed.

Pressure measuring device 47 is a pressure sensor as is known to those skilled in the art that is capable of measuring the pressure exerted by the confining fluid 23 on the rigid wall 29. In a preferred embodiment, the pressure measuring device 47 is a Sensotec 0–5 psi Model PPG/6846-01 (order code PPG61AT,2U5A6Q45X) as manufactured by Honeywell sensotec of Columbus, Ohio USA. The sensor 47 is preferably calibrated to a plus/minus 1mm water head degree of accuracy. However, any pressure sensor known to those skilled in the art that capable of measuring fluid pressure to the degree of sensitivity and accuracy required may be employed.

Referring to FIGS. 1, 2(a)–(b), 3 and 6(a)–(d), the confining chamber 13 has a top sealing member 49 and a bottom sealing member 51 that together with the confining chamber 13 define a confining chamber cavity. In a preferred embodiment, the top sealing member 49 is a chamber engaging end of a permeant reservoir 53. The permeant reservoir 53 is sealingly mounted to the top end 17 of the chamber 13. A chamber top groove 55 is machined in the top end 17 for receiving an o-ring 63, and a corresponding reservoir groove 57 is machined in the chamber engaging end of the reservoir 53. The reservoir 53 is then secured to the chamber 13. The chamber engaging end preferably defines a bevelled surface 59 that facilitates the removal of air from the confining chamber 13 via a vent 61.

In a present embodiment of the invention, the reservoir 53 is bolted to the chamber 13. However, any means, known to those skilled in the art, for securing the reservoir 59 to the chamber 13 and thereby enabling the o-ring 63 to act as a seal for preventing the confining fluid 23 to pass therebetween may be employed.

In an alternate embodiment, the top end 17 and chamber engaging end of the reservoir 53 do not have grooves 55 and 57, but rather are secured together using a sealing ring or screw means. As will be apparent, any sealing means known to those skilled in the art that can sealingly secure the chamber 13 to the reservoir 53 may be employed.

The reservoir 53 holds the permeant 37 that is supplied to the top member 21. In an embodiment, it further includes a connection 65 to a pressure sensor 67, thereby permitting constant monitoring of the permeant 37 pressure applied to the sample 99 during testing. The pressure sensor 67 may be any pressure sensor known to those skilled in the art that is able to provide a reading representative of fluid pressure.

In the present invention, the sensor is a Senstotec 0–5 psi Model PPG/6846-01 (order code PPG61AT,2U5A6Q45X) as manufactured by Honeywell Sensotec of Columbus Ohio, USA. The sensor 67 is preferably calibrated to a plus/minus 1mm water head degree of accuracy. However, any pressure sensor known to those skilled in the art that capable of measuring fluid pressure to the degree of sensitivity and accuracy required may be employed.

Figure 3:
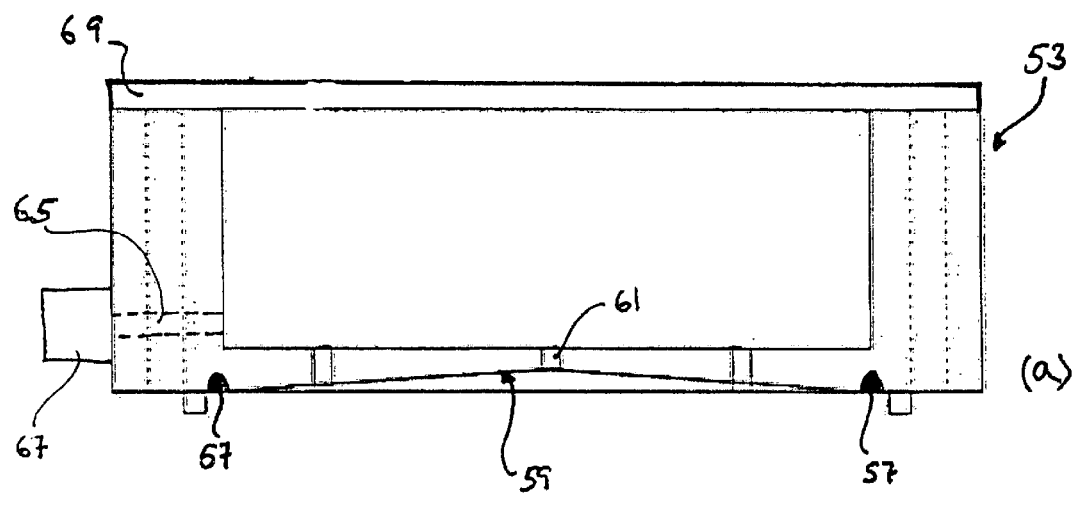
FIG. 3(a) is a sectional view of a permeant reservoir of the apparatus of FIG. 1 according to an embodiment of the present invention.
FIG. 3(b) is a plan view of the permeant reservoir of FIG. 3(a)
Figure 3:
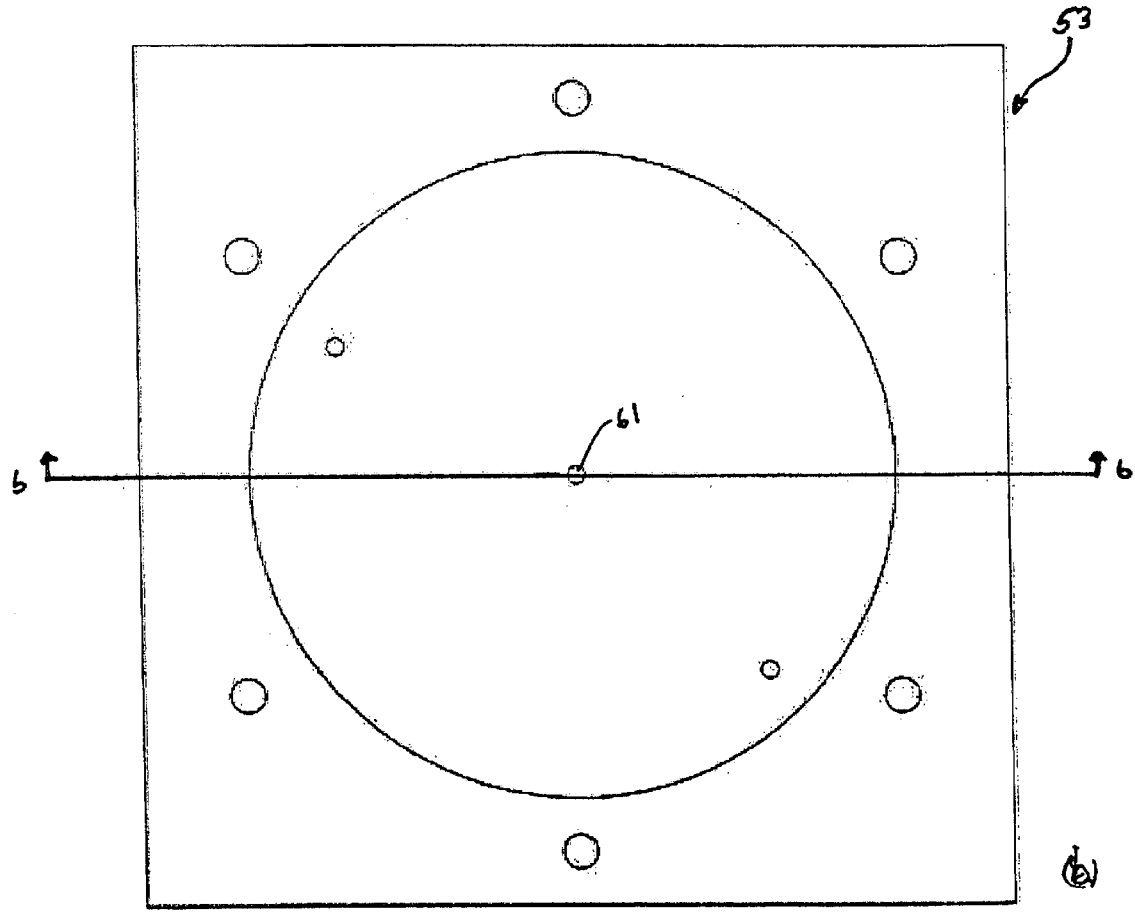
Figure 5:
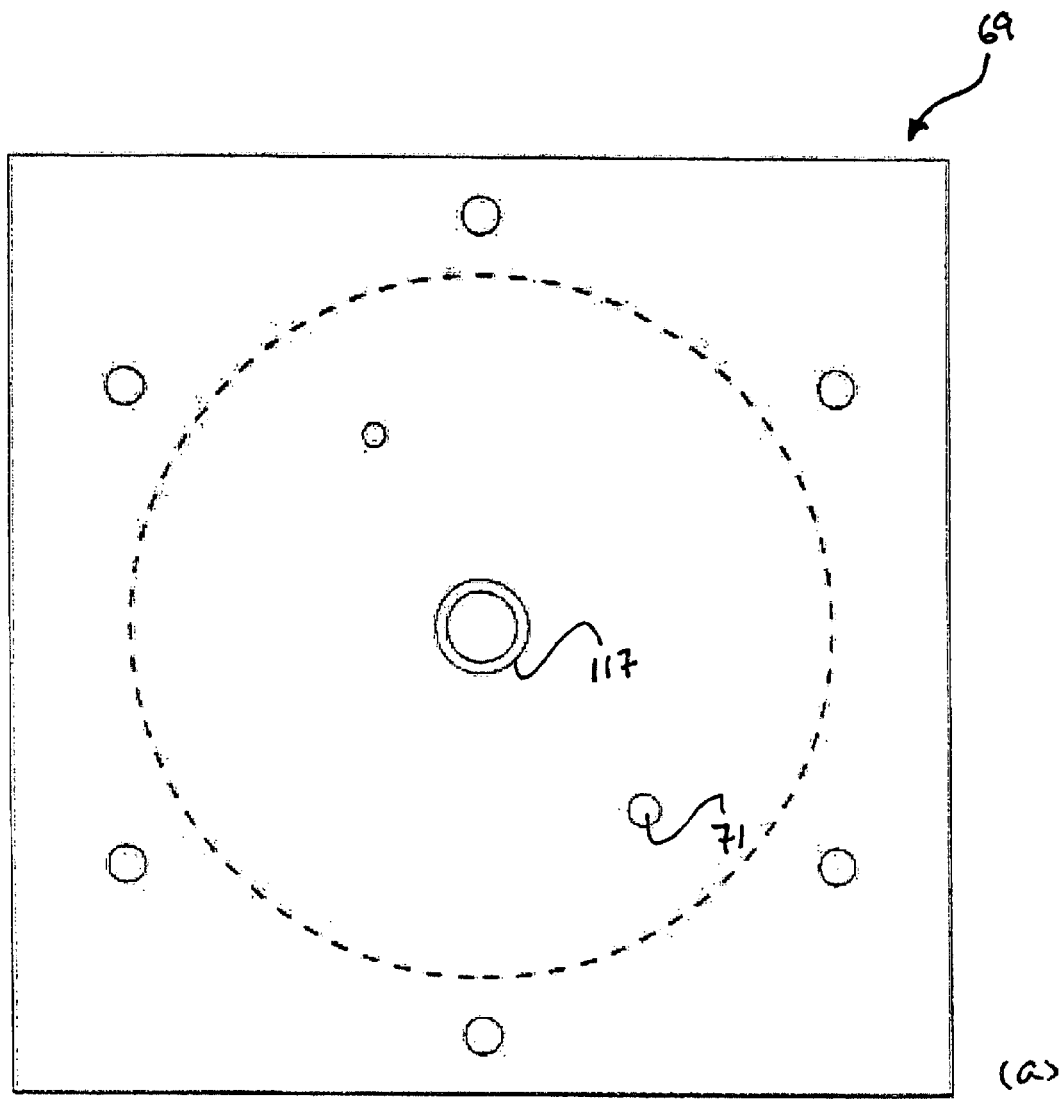
FIG. 5(a) is a plan view of a lid for the permeant reservoir of FIG. 3(a)
FIG. 5(b) is an end view of the lid of FIG. 5(a)
Figure 5:
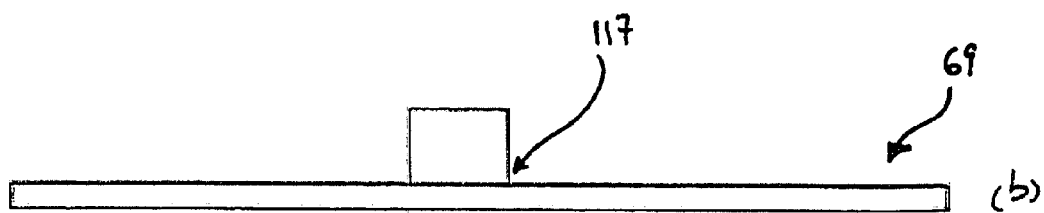

Referring to FIGS. 3 and 5, the reservoir 53 also includes a reservoir top 69, which may be configured to support any top mounted monitoring equipment. The reservoir top 69 additionally includes a fill port 71 for adding or removing the permeant 37.

Referring to FIGS. 1, 2(a)–(b) and 4, according to a preferred embodiment, the bottom sealing member SI is a chamber engaging end of the permeant accumulator or collection chamber 41. The collection chamber 41 is sealingly mounted on the bottom end 19 of the chamber 13. In a preferred embodiment of the present invention, a groove 73 is machined in the bottom end 19 for receiving an o-ring 75, and a corresponding groove 77 is machined in the chamber engaging end of the collection chamber 41. The collection chamber 41 is then secured to the chamber 13.

In a present embodiment of the invention, the collection chamber 41 is bolted to the chamber 13. However, any means, known to those skilled in the art, for securing the collection chamber 41 to the chamber 13 and thereby enabling the o-ring 75 to act as a seal for preventing the confining fluid 23 to pass therebetween may be employed.

In an alternate embodiment, the bottom end 19 and the chamber engaging end of the collection chamber 41 do not have grooves 73 and 77, but rather are secured together using a sealing ring or screw means. However, it will be apparent that any sealing means known to those skilled in the art that can sealingly secure the chamber 13 to the collection chamber 41 may be employed.

Referring to FIGS. 1, 6(a)–(d) and 12, the resilient inner sleeve 31 is positioned within the rigid outer sleeve 29 and mountable over the sample 99. In a preferred embodiment, the resilient inner sleeve 31 forms a flexible boundary surrounding the sample 99 and conforms to any surface irregularities on the sample 99. The inner sleeve 31 is comprised of a resilient material, such as latex. However, any resilient material know to those skilled in the art that can form a flexible boundary surrounding the sample 99 and is non-reactive with the confining fluid 23 or the permeant 37 may be employed.

The sample 99 rests on a base member 79, which is a preferred embodiment of the present invention is connected to the chamber engaging end of the collection chamber engaging end of the collection chamber 41. In an alternate embodiment, the base member 79 may form an integral part of the chamber 13.

The base member 79 may be releasably connected to the chamber engaging end of the collection chamber 41 by any means known to those skilled in the art, thereby permitting the use of base members 79 of varying sizes to accommodate samples 99 of varying sizes.

The top member 21 is positioned on the top face 97 of the sample 99. In a preferred embodiment of the present invention, the top 21 is moveable with the sample 99 during operation of the centrifugal permeameter. Accordingly, tops 21 of varying sizes may be employed to accommodate different sample 99 sizes.

The top 21 supplies and distributes the permeant 37 to the sample 99. It receives the permeant 37 from the permeant supply 39.

In a preferred embodiment, the permeant supply 39 is comprised of the permeant reservoir 53 and a permeant supply tube 83, which connects to the reservoir 53 and top 21 and permits permeant delivery to the top 21. The permeant supply tube 83 is prefereably a semi-rigid material that is resistant to volume and pressure changes in the surrounding confining fluid 23, but flexible enough to allow the top 21 to move freely during operation of the centrifugal permeameter.

In the present embodiment, the permeant supply tube 83 is constructed of polythene or nylon. Alternatively, any material known to those skilled in the art that permits delivery of permeant from the reservoir 53 to the top 21 and is rigid enough to be resistant to volume and pressure changes may be employed.

Figure 7:
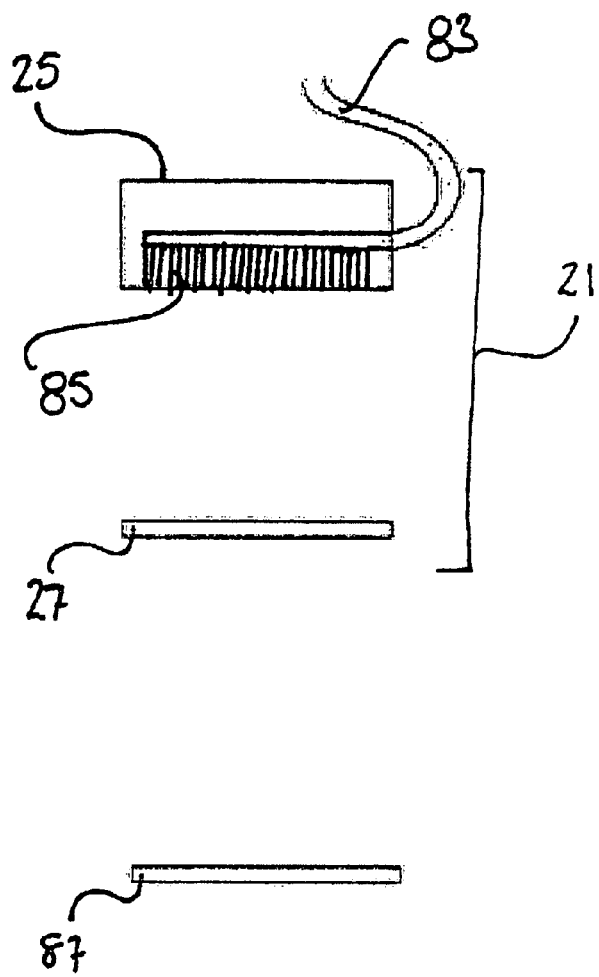
FIG. 7 is an exploded view of a top member for the apparatus of FIG. 1 according to an embodiment of the present invention.

Referring to FIGS. 1 and 7, a schematic cross-sectional view of the top member 21 is illustrated according to a preferred embodiment of the present invention. The top member 21 is comprised of a top cap 25 and an underlying upper porous material 27. The top cap 25 distributes the permeant 37 received from the permeant supply means 39 to the top surface 97 of the sample 99 via the upper porous material 27. In a preferred embodiment, the top cap 25 includes channels 85, which distribute the permeant 37 freely about the top cap 25, and as a result the upper porous material 27.

The mass of the top cap 25 is such that it does not produce any appreciable vertical consolidation of the sample 99. In a preferred embodiment, the top cap 25 is comprised of a plastic, lucite, glass, metal or combinations thereof. However, any rigid material known to those skilled in the art that has a mass or density that would not result in any appreciable vertical consolidation of the sample 99 may be employed.

The upper porous material 27 is positioned between the top cap 25 and the top surface 97 of the sample 99. It is comprised of a porous medium through which the permeant 37 diffuses freely and is deposited on the sample 99. The mass of the upper material 27 is preferably such that it does not produce any appreciable vertical consolidation of the sample 99.

In a preferred embodiment, the upper material 27 is constructed from porous stone, geomembrane, filter paper, or combinations thereof, such as porous stones ELE 25-5561 having high water permeability and low air entry pressure alundum or bronze as manufactured by ELE International UK of the United Kingdom. However, any material known to those skilled in the art that has a mass or density that would not result in any appreciable vertical consolidation of the sample 99 and provides a porous medium through which permeant 37 diffuses freely may be employed. The material out of which the upper material 27 is constructed is also selected to have a permeant conductivity greater than that of the sample 99 being tested, so as to ensure that the permeant conductivity of the sample 99 is being measured, not the permeant conductivity of the upper material 27.

A lower porous material 87 is positioned between the sample 99 and the base pedestal or member 79. It acts as a conduit that transmits the permeant 37, which has passed through the sample 99 during testing, from the base of the sample 99 to the collection chamber 41.

In a preferred embodiment of the present invention, the lower porous material 87 is comprised of a porous medium through which the peremeant 37 may be transmitted freely and is preferably constructed from one of porous stone, geomembrane, filter paper or combinations thereof, such as porous stones ELE 25-5561 having high water permeability and low air entry pressure alundum or bronze as manufactured by ELE International UK of the United Kingdom.

The permeant conductivity of the lower material 87 is greater than that of the sample 99 and the upper material 27. In a preferred embodiment, the permeant conductivity of the lower material 87 is at least an order of magnitude greater than that of the sample 99. Unlike the upper material 27, there is no mass restriction for the lower material 87 since the sample 99 sits on the lower material 87 and as such there is no concern for vertical displacement of the sample 99.

Figure 6:
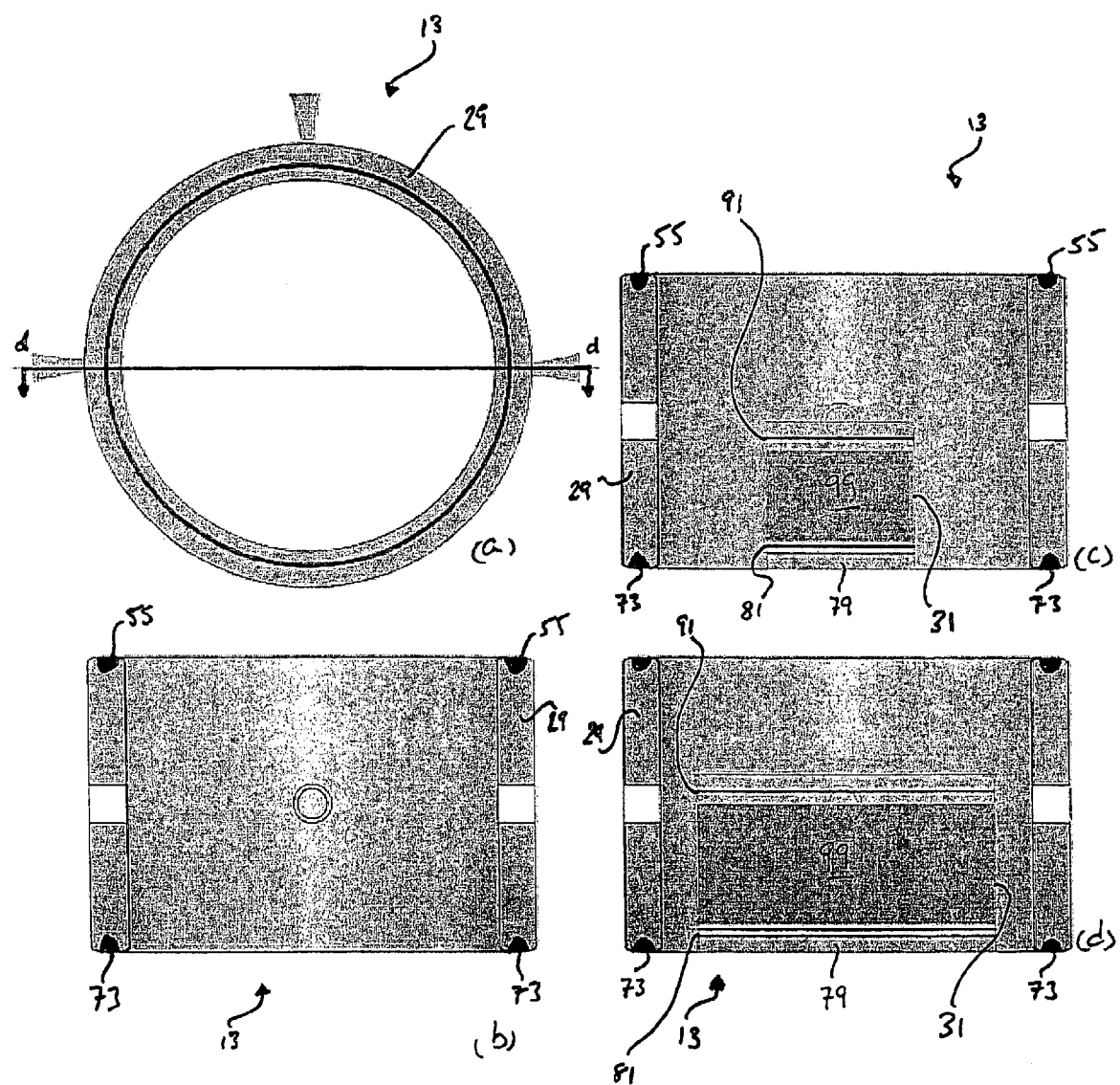
FIG. 6(a) is a plan view of the confining chamber of the apparatus of FIG. 1 according to an embodiment of the present invention.
FIG. 6(b) is a sectional view of the confining chamber of FIG. 6(a)
FIG. 6(c) is a sectional view of the confining chamber of FIG. 6a illustrating a first sample and resilient inner sleeve according to an embodiment of the present invention.
FIG. 6(d) is a sectional view of the confining chamber of FIG. 6a illustrating a second sample and resilient inner sleeve according to an embodiment of the present invention.
Figure 8:
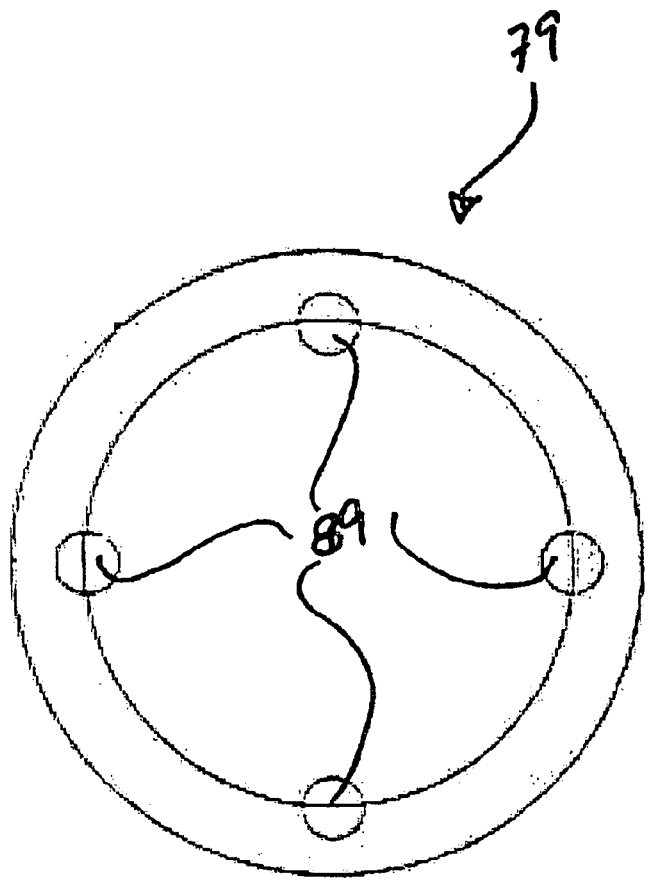
FIG. 8 is a plan view of a base member of the apparatus of FIG. 1 according to an embodiment of the present invention.

Referring to FIGS. 1, 6 and 8, the base pedestal 79 is of a size sufficient to support the sample 99. It is also provided with a series of drain holes or drainage channels 89 that permits transfer of the permeant 37 from the lower porous material 87 to the collection chamber 41.

In a preferred embodiment, the base pedestal 79 is secured to the collection chamber 41 via screw means, thereby permitting base pedestals 79 of varying sizes to be secured to the collection chamber 41. However, any releasable securing means that permits base pedestals of varying sizes to be secured to the collection chamber may be employed.

Referring to FIGS. 1, 6(a)–(d) and 12, a sectional view of the resilient inner sleeve 31 and associated elements is illustrated. The inner sleeve 31 provides a barrier that separates the sample 99 from the surrounding confining fluid 23. This barrier is provided by having seal means 35 between the inner sleeve 31 and the top cap 25 and between the inner sleeve 31 and the base pedestal 79.

In a present embodiment of the invention, the sealing means 35 is provided by o-rings 91 and 81, respectively. The top o-ring 91 is selected to have a circumference sufficiently less than the circumference of the top cap 25 so as to secure the inner sleeve 31 to the top cap 25 with a force sufficient to ensure a confining- fluid 23 resistant barrier and prevent intermixing of the fluid 23 and permeant 37.

The base o-ring 81 is selected to have a circumference sufficiently less than the circumference of the pedestal 79 so as to secure the inner sleeve 31 to the base pedestal 79 with a force sufficient to ensure a confining fluid 23 resistant barrier and prevent intermixing of the fluid 23 and permeant 37.

In an alternate embodiment of the present invention, the o-rings 811 and 91, may form integral elements of the inner sleeve 31. However, it will be readily apparent that any sealing means 35 known to those skilled in the art that are able to form a barrier preventing intermixing of the confining fluid 23 and permeant 37.

Figure 4:
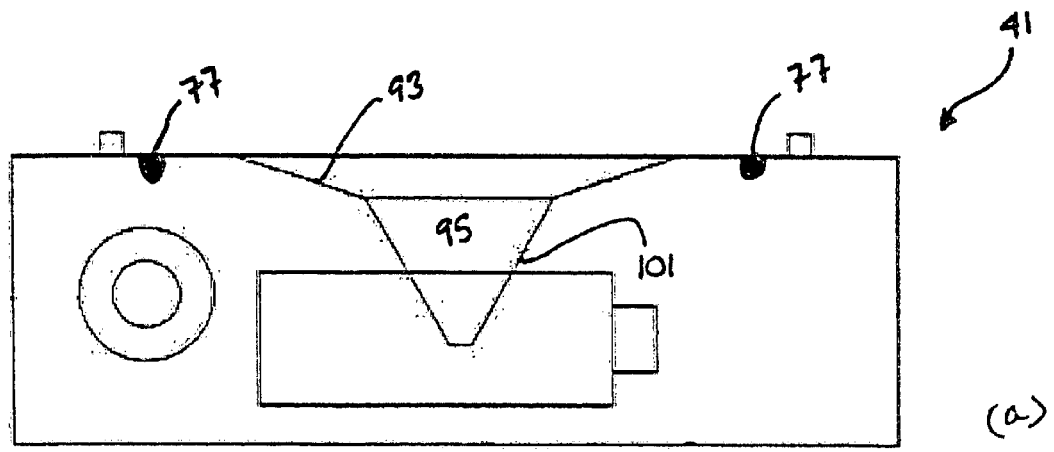
FIG. 4(a) is a sectional view of a collection chamber of the apparatus of FIG. 1 according to an embodiment of the present invention.
FIG. 4(b) is a plan view of the chamber of FIG. 4(a)
Figure 4:
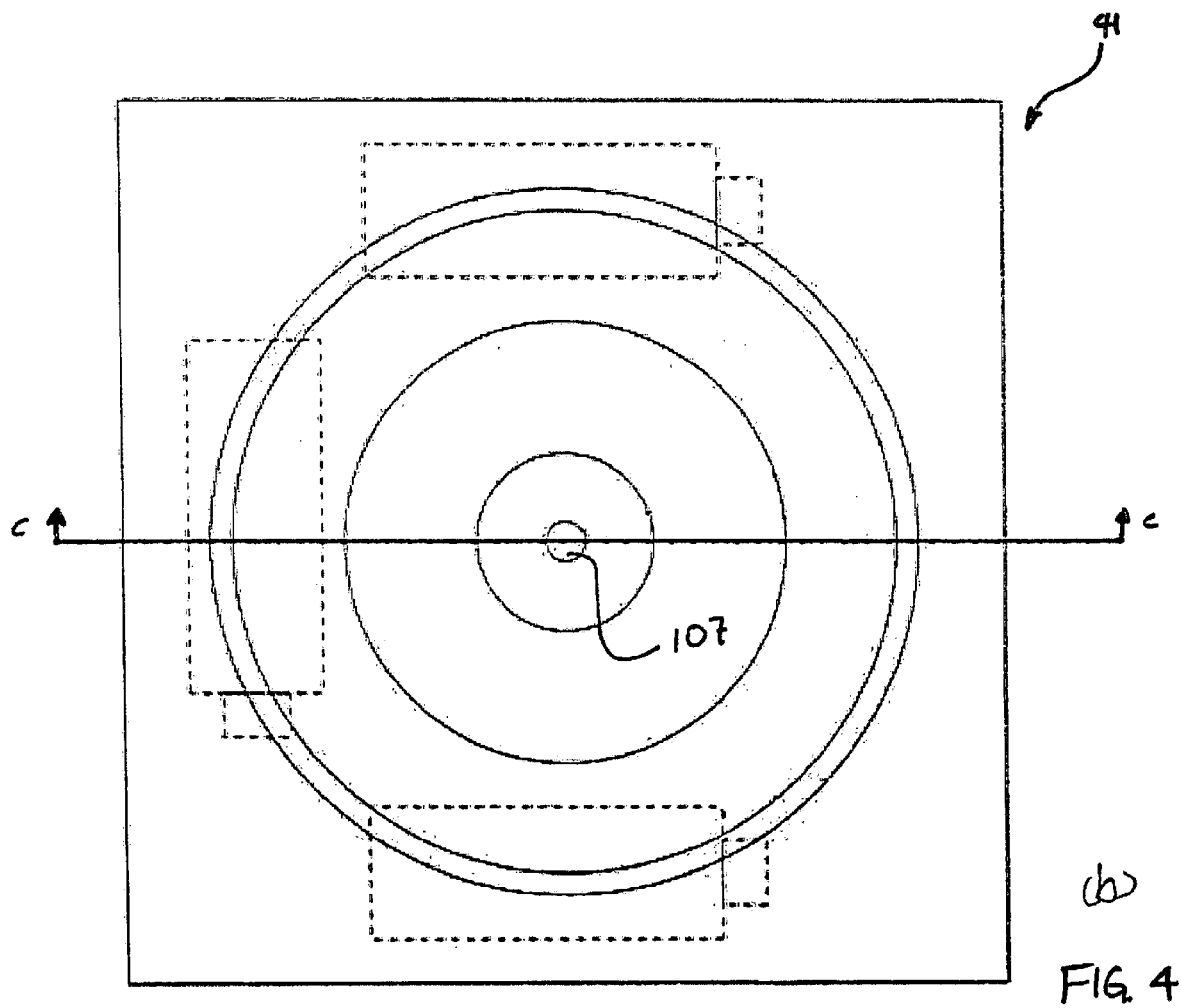
Figure 9:
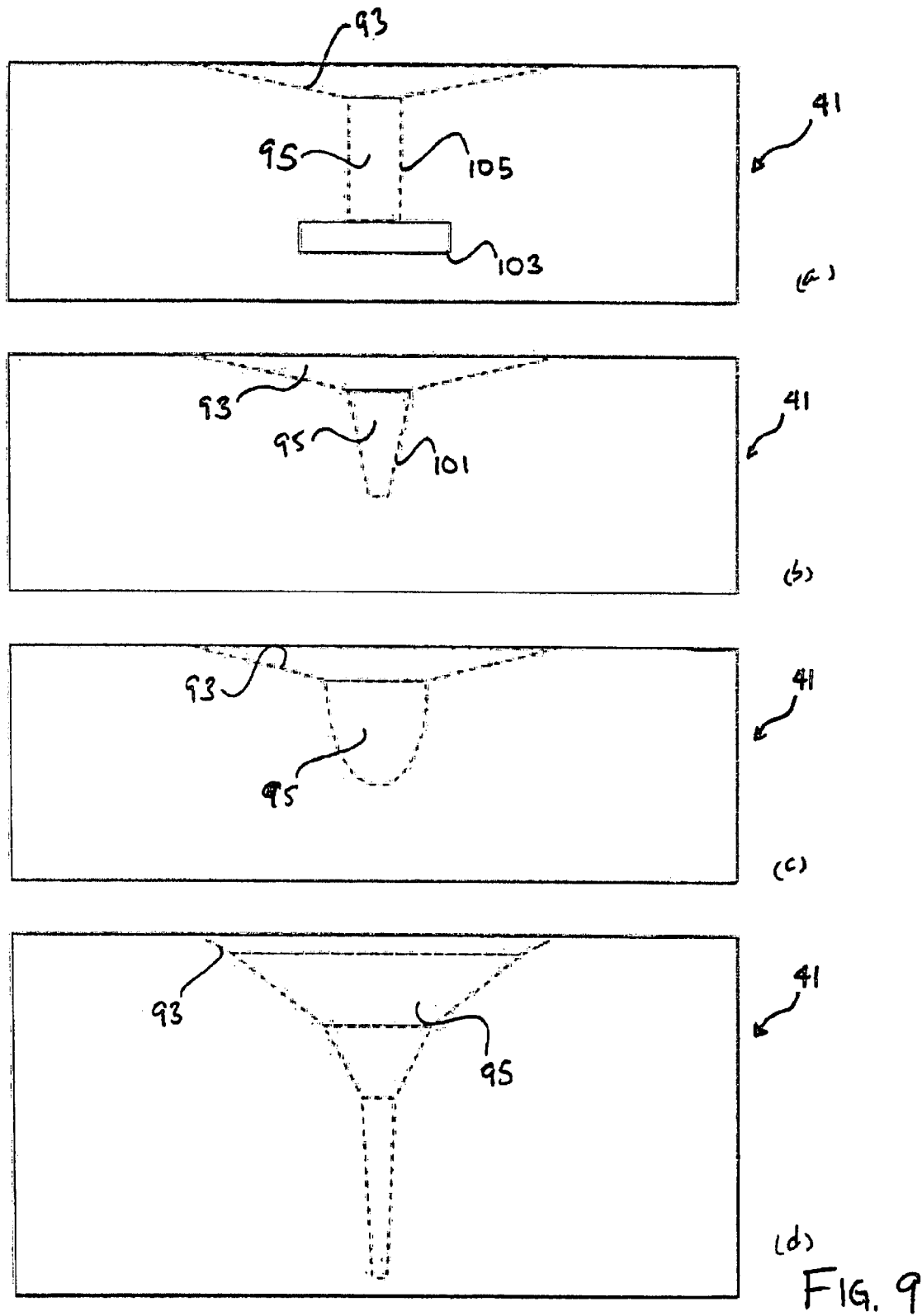
FIGS. 9(a)–(d) are sectional views of the collection chamber of FIG. 4(a) according to further embodiments of the present invention.
Figure 10:
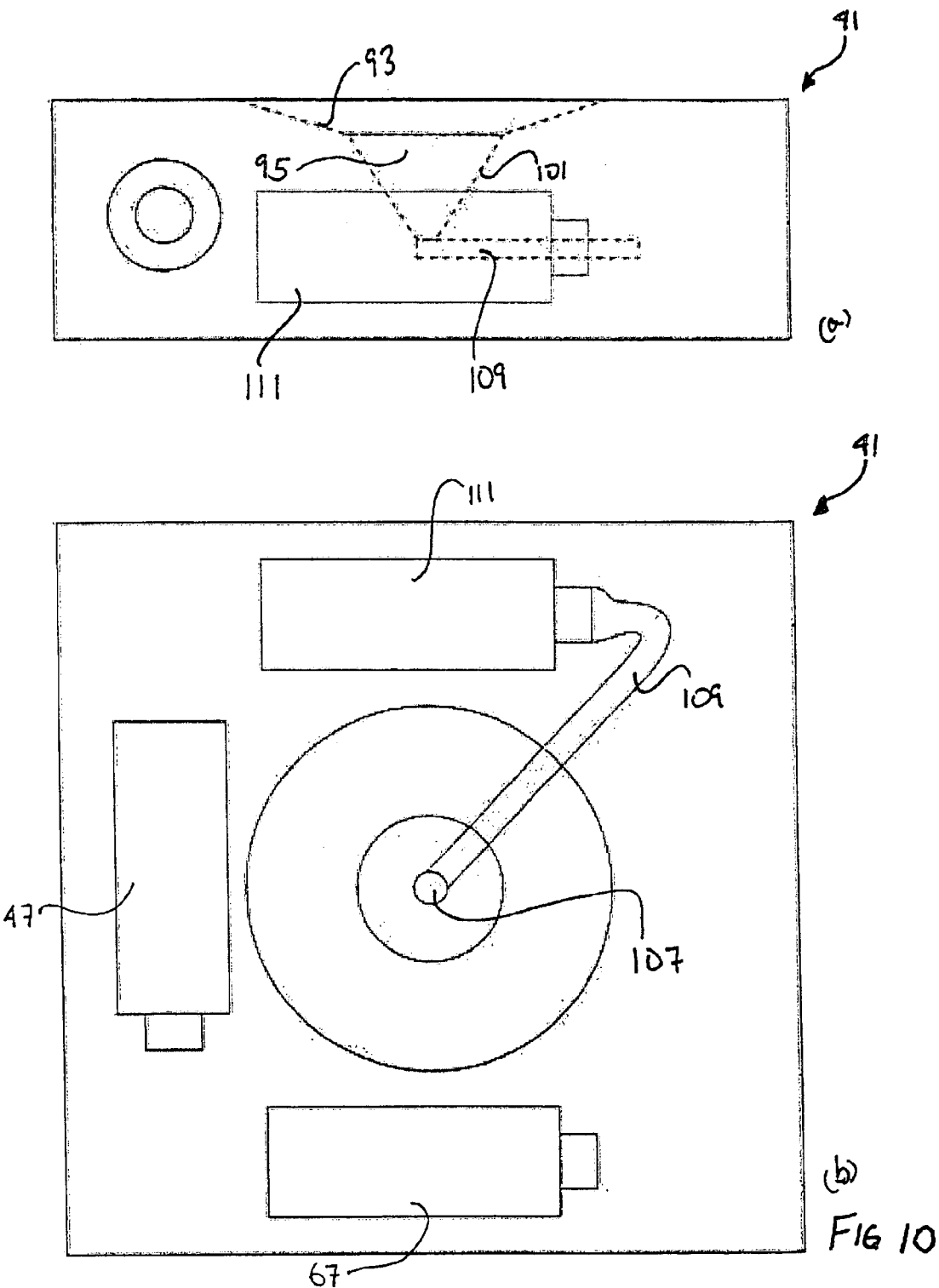
FIG. 10(a) is a sectional view of the collection chamber of FIG. 4(a) according to a still further embodiment of the present invention.
FIG. 10(b) is a plan view of the collection chamber of FIG. 10(a)

Referring to FIGS. 4, 9 and 10, the collection chamber 41 is illustrated according to a preferred embodiment of the present invention. The collection chamber 41 includes permeant receiving means, for receiving the permeant that has passed through the sample 99 during testing, which is comprised of a permeant flow guide 93 that directs the permeant 37 to a volume collector 95.

In a present embodiment, the flow guide 93 is a machined bevelled surface positioned opposite the drainage channels 89 of the base pedestal 79. As the permeant 37 passes through the drainage channel 89 it is received by the flow guide 93, which in turn directs the permeant 37 to the volume collector 95.

The volume collector 95 coupled with measuring means determines the volume of permeant 37 that has passed through the test sample 99 and ultimately the permeant conductivity of the sample 99. The geometry of the volume collector 95 is largely determined by the type of measuring means employed. For example, if a high accuracy high precision pressure sensor is used, then the geometry selected for the volume collector 95 should ensure an accurate volume to height ratio, such as a cone 101. Alternately, if a load sensing device 103, is used, the geometry of the volume collector 95 is selected to ensure that the full volume of the permeant 37 that has passed through the test sample 99 rests on the sensing device 103, such as a cylinder 105.

In a present embodiment, the volume collector 95 further includes an outlet port 107 at its base. A connection passage 109 provides for permeant communication of the volume collector 95 with its associated measuring means, pressure sensor 111. Preferably, the connection passage 109 is constructed to permit one-way permeant flow, so as to ensure that permeant 37 cannot re-enter the passage 109. The pressure sensor 111 provides electronic means by which the height of the collected permeant column is determined.

In a preferred embodiment, the collection chamber 41 further includes the confining fluid pressure sensor 47 for monitoring and measuring the pressure of the confining fluid 23, within the confining chamber 13, and the permeant pressure sensor 67 for monitoring and measuring the pressure of the permeant 37 within the reservoir 53, i.e., the permeant pressure being applied to the test sample 99. The sensors 47 and 67 are connected to respective confining chamber 13 and reservoir 53 by respective connection passages.

Referring to FIGS. 1, and 5 any vertical consolidation of the sample 99 occurring during testing (as a result of any one of the weight of the top member 21 or the testing pressure of the permeant 37) may be measured by a vertical displacement sensor 113. The vertical displacement sensor 113 is an electronic device as is known to those skilled in the art that directly measures changes in the vertical dimension of the test sample 99, while at the same time not transmitting any significant vertical load to the sample 99.

In the present embodiment, the vertical displacement sensor 113 sits atop the reservoir top 69. It is connected to the top cap 25 via a displacement rod 115, which passes through the reservoir top 69 at a vertical displacement housing 117 and also passes through the reservoir 53. The displacement rod 115 is connected to the top cap 25, such that during testing, as vertical consolidation of the sample 99 occurs, the top cap 25 and rod 115 move with the sample 99. The vertical displacement sensor 113 determines the degree of vertical displacement of the sample 99 that has occurred.

Figure 11:
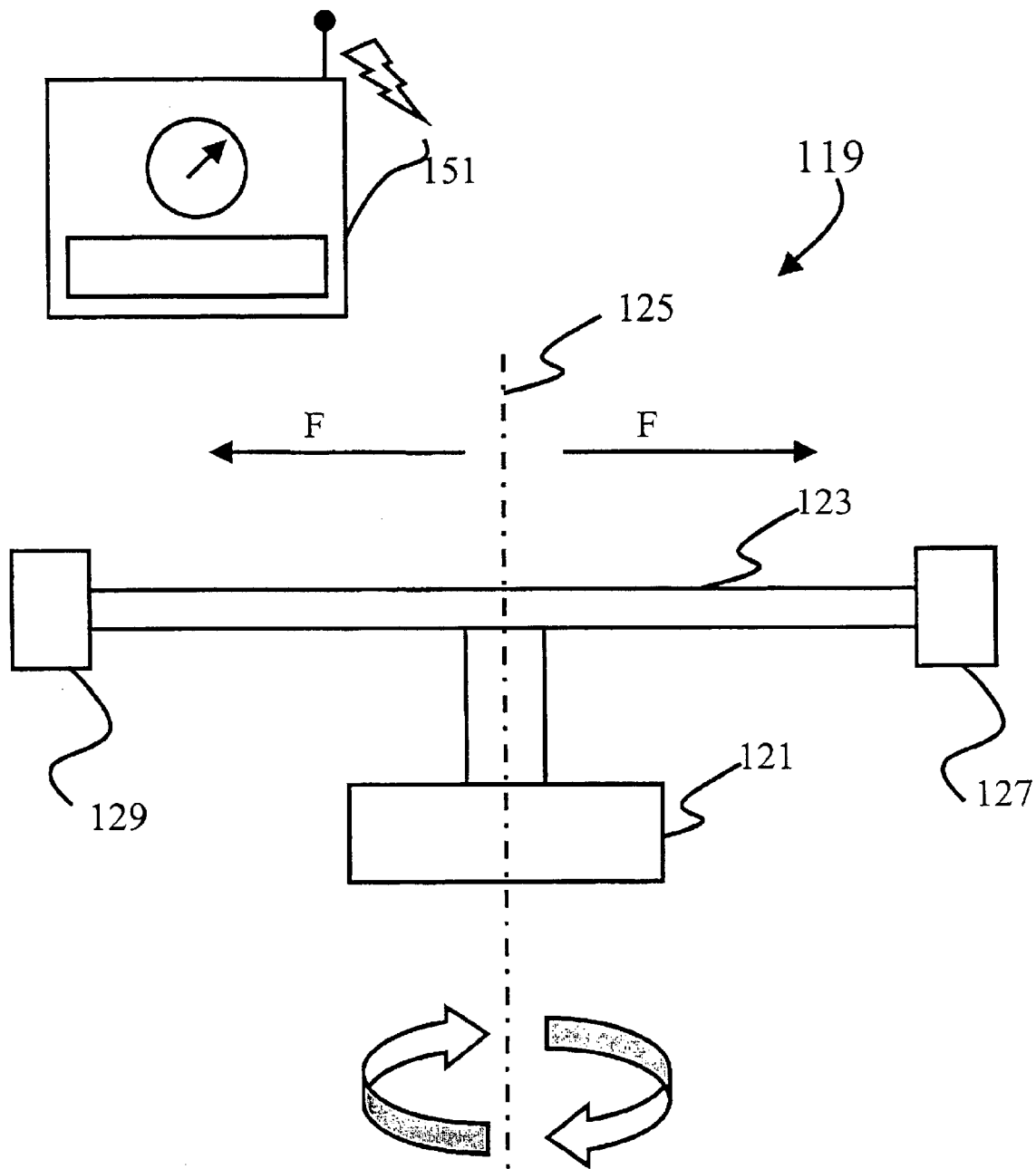
FIG. 11 is a schematic view of a centrifugal permeameter according to an embodiment of the present invention.
Figure 12:
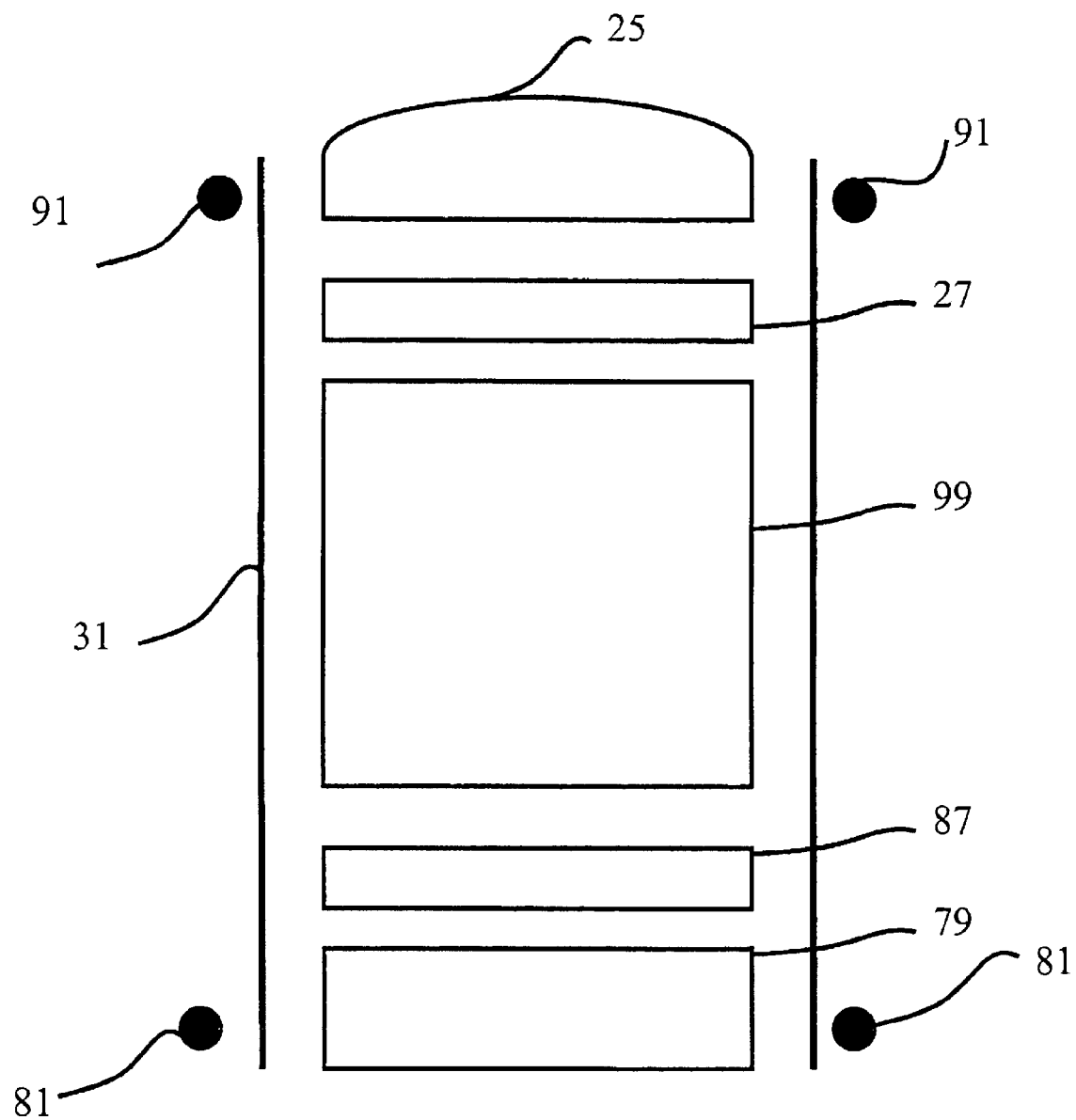
FIG. 12 is an exploded schematic sectional view of the resilient inner sleeve secured to the top member and base member of the apparatus of FIG. 1 according to an embodiment of the present invention; and, FIG. 13 is a graphic comparison of permeant conductivity test results generated by the apparatus of FIG. 1 to test results generated by a triaxial cell bench permeameter.

Referring to FIG. 11, a centrifugal permeameter 119 according to an embodiment of the present invention is illustrated. The permeameter 119 includes a base 121, a support arm 123 extending from the base 121, which rotates about an axis 125. A sample chamber housing 127 is mounted to one end of the arm 123 and a counterweight 129 is mounted to an opposite end of the arm 123. When the permeameter 119 is in operation, a centrifugal force (F) is generated, the direction of which is normal to the axis of rotation 125. It is the centrifuge 119 that permits scaling of gravity, which is proportional to the ratio of the applied centrifugal acceleration to the earth's gravitational constant (g). The direction of the force F exerted on the sample chamber 10 is illustrated in FIG. 1 by reference letter F. The force F determines the force that the permeant 37 exerts on the sample 99.

During operation of the centrifuge 119, the pressure or force exerted by the permeant 37 on the sample 99 is monitored and measured by the permeant pressure sensor 67, the output of which is communicated to a receiver-processor 151 to determine a gravity scaling number and also to monitor any variations in the permeant force (and as a result the gravity scaling number) during the testing period.

As the permeant 37 passes through the sample 99, it is directed to the permeant accumulator 41 and the volume of the permeant 37 that has passed is measured by one of a load sensing device 103 or volume pressure sensor 111. As in the case of the permeant pressure sensor 67, the volume of the permeant that passes through the sample 99 during testing may be continuously or intermittently monitored by one of the device 103 or sensor 111, and communicated to the receiver-processor 151. This permits any variations in the permeant 37 flow to be monitored during the testing period.

The pressure exerted on the sample 99 by permeant 37 is also used to determine the confining fluid 23 pressure in the chamber 13 that is necessary to ensure that the permeant does not pass along the surface of the sample 99 between the sample 99 and the inner sleeve 31. The pressure of the confining fluid 23 is measured and monitored by the confining pressure sensor 47, which communicated this measurement to the receiver-processor 151. The confining fluid pressure is selected to be sufficiently high to generate a compressive confining fluid force that prevents movement of the permeant 37 between the surface of the sample 99 and the inner membrane 31 and thereby restricts flow of the permeant to the body of the porous ample 99. The data collected from the confining pressure sensor 47 and the permeant pressure sensor 67 allows the pressure of the confining fluid 23 to be adjusted accordingly in response to any variation in the permeant pressure so as to ensure that the permeant flows through only the body of the sample 99.

The information collected by the vertical displacement sensor 113 may be used to determine the degree of vertical consolidation that occurs to the sample 99 during testing. This information may be used to, for example, fine tune the selection of the appropriate building materials for the sample chamber components (e.g., top cap 25) or to adjust permeant force exerted in the sample 99.

The output of the permeant pressure sensor 67 and the load sensing device 103 or volume pressure sensor 111 may be used to determine the permeant conductivity of the sample 99. Variations in permeant 37 pressure (the out put of the permeant sensor 67) and confining fluid pressure (output of the confining fluid pressure sensor 47) in conjunction with any sample 99 consolidation (output of the vertical displacement sensor 113) may be used to assess the quality of the test results.

Figure 13:
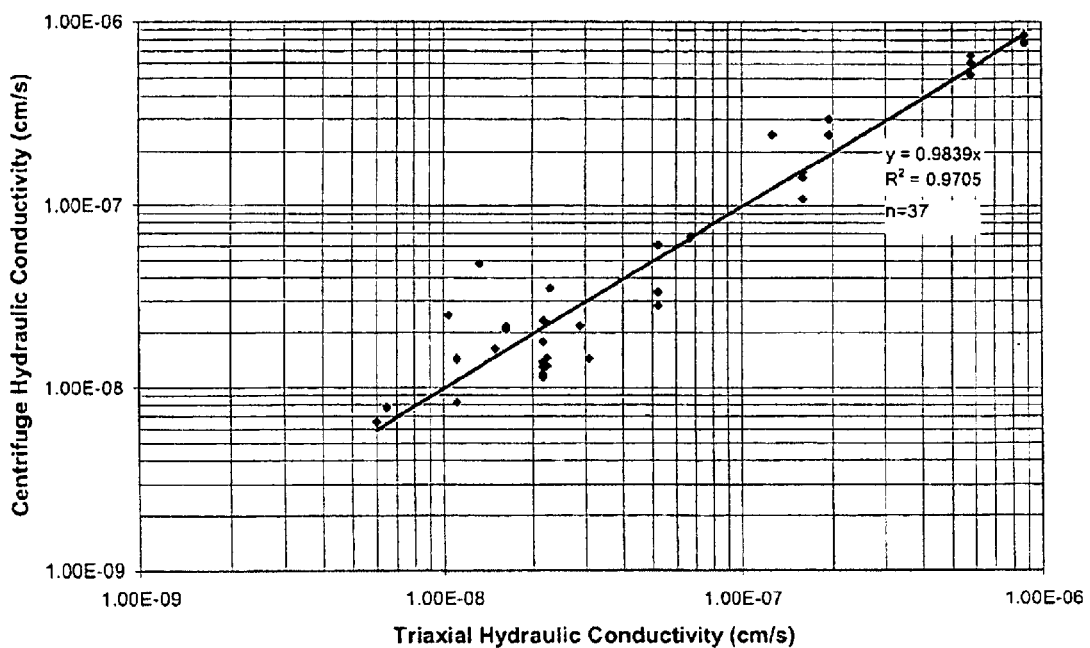

A second measure of the quality of the permeant conductivity test results generated by the apparatus 10 is illustrated in FIG. 13, a graphical comparison of permeant conductivity test results generated by the apparatus 10 to test results of identical samples generated by a current benchmark testing methodology, a triaxial cell bench permeameter. The test results demonstrate a high correlation of the apparatus 10 test results to the triaxial permeameter test results.

Although the invention has been described with reference to certain specific embodiments, various modifications thereof will be apparent to those skilled in the art without departing from the spirit and scope of the invention as outlined in the claims appended hereto.

We claim:

1. A sample chamber for a centrifugal permeameter for testing permeant conductivity of a porous sample, said sample chamber comprising:

a rigid outer sleeve;

a resilient inner sleeve mountable over said sample and within said rigid outer sleeve;

fluid inlet means for introducing fluid between said inner and outer sleeves;

sealing means acting between said inner and outer sleeves for maintaining said fluid therebetween;

a porous top member for mounting over a top face of said sample and supplying said permeant to said sample, said top being movable with said sample to maintain a radially outward permeant force on said sample as said sample is being spun in said centrifugal permeameter;

a permeant supply for supplying said permeant to said porous top; and, a permeant accumulator for receiving and accumulating permeant which has passed through said sample.

2. The sample chamber of claim 1 further having a sensor in fluid communication with said permeant supply for sensing pressure exerted by said permeant on said sample and sending a signal to a receiver indicative of said exerted permeant pressure during centrifuging.

3. The sample chamber of claim 1 further having a sensor for determining a degree of sample consolidation exhibited by said sample during centrifuging and sending a signal to a receiver indicative of said degree of sample consolidation during centrifuging.

4. The sample chamber of claim 1, wherein the rigid outer sleeve is comprised of one of plastic, metal and glass.

5. The sample chamber of claim 1, wherein the resilient inner sleeve is comprised of latex.

6. The sample chamber of claim 1, wherein the sealing means are o-ring sealing means.

7. The sample chamber of claim 1, wherein the porous top member comprises a top cap and an underlying porous material having a permeant conductivity greater than that of the sample.

8. The sample chamber of claim 1 further having a sensor for sensing changes in at least one of pressure and volume in said fluid between said inner and outer sleeves and sending a signal to a receiver indicative of said volume change during centrifuging.

9. The sample chamber of claim 1 having a sensor in said accumulator for determining an amount of said permeant which has permeated said sample and sending a signal to a receiver indicative of said amount during centrifuging.

10. A The sample chamber of claim 8 or 9 further having a sensor in fluid communication with said permeant supply for sensing pressure exerted by said permeant on said sample and sending a signal to said receiver indicative of said exerted permeant pressure during centrifuging.

11. The sample chamber of claim 8 further having a sensor in said accumulator for determining an amount of said permeant which has permeated said sample and sending a signal to said receiver indicative of said amount during centrifuging.

12. The sample chamber of claim 11 further having a sensor in fluid communication with said permeant supply for sensing pressure exerted by said permeant on said sample and sending a signal to said receiver indicative of said exerted permeant pressure during centrifuging.

13. The sample chamber of claim 12 further having a sensor for determining a degree of sample consolidation exhibited by said sample during centrifuging and sending a signal to said receiver indicative of said degree of sample consolidation during centrifuging.

14. The sample chamber of claim 13 further having comparing and adjusting means for comparing said changes in said at least one of pressure and volume of said fluid between said inner and outer sleeves to said pressure exerted by said permeant on said sample and adjusting said at least one of pressure and volume of said fluid between said inner and outer sleeves by a degree sufficient to restrict movement of said permeant to said porous sample.

* * * * *